United States Patent [19]
Guttman et al.

[11] Patent Number: 5,370,777
[45] Date of Patent: Dec. 6, 1994

[54] CAPILLARY COLUMN CONTAINING REMOVABLE SEPARATION GEL COMPOSITION AND METHOD OF USE

[75] Inventors: Andras Guttman, Palo Alto; Chia-Hui Shieh, Irvine, both of Calif.; Barry L. Karger, Newton, Mass.; Stephen J. Pentoney, Jr., Yorba Linda, Calif.; Kenneth D. Konrad, Long Beach, Calif.; Sushma Rampal, Yorba Linda, Calif.; Katalin Ganzler, Melrose, Mass.

[73] Assignee: Beckman Instruments, Inc., Fullerton, Calif.

[21] Appl. No.: 884,101

[22] Filed: May 15, 1992

Related U.S. Application Data

[63] Continuation-in-part of Ser. No. 829,638, Jan. 31, 1992, Pat. No. 5,213,669.

[51] Int. Cl.$^5$ .................. G01N 27/26; G01N 27/447
[52] U.S. Cl. ............................... 204/182.8; 204/180.1; 204/299 R
[58] Field of Search .............. 204/299 R, 180.1, 182.8

[56] References Cited

U.S. PATENT DOCUMENTS

| | | | |
|---|---|---|---|
| 4,657,656 | 4/1987 | Ogawa | 204/299 R |
| 4,680,201 | 7/1987 | Hjerten | 427/230 |
| 4,729,947 | 3/1988 | Middendorf et al. | 435/6 |
| 4,865,706 | 9/1989 | Karger et al. | 204/182.8 |
| 4,865,707 | 9/1989 | Karger et al. | 204/182.8 |
| 4,959,134 | 9/1990 | Gross et al. | 204/182.8 |
| 4,962,020 | 10/1990 | Tabor et al. | 435/6 |
| 4,997,537 | 3/1991 | Karger et al. | 204/182.8 |
| 5,011,769 | 4/1991 | Duck et al. | 435/6 |
| 5,015,350 | 5/1991 | Wiktorowicz | 204/180.1 |
| 5,045,172 | 9/1991 | Guzman | 204/299 |
| 5,061,336 | 10/1991 | Soane | 156/245 |
| 5,064,519 | 11/1991 | Tice, Jr. et al. | 240/182.8 |
| 5,068,176 | 11/1991 | Vijg et al. | 435/6 |
| 5,089,111 | 2/1992 | Zhu et al. | 204/180.1 |
| 5,096,554 | 3/1992 | Chin | 204/180.1 |
| 5,098,539 | 3/1992 | Shieh | 204/182.8 |
| 5,110,424 | 5/1992 | Chin | 204/180.1 |

FOREIGN PATENT DOCUMENTS

| | | | |
|---|---|---|---|
| 0442177 | 8/1991 | European Pat. Off. | B01D 57/02 |
| WO91/11709 | 8/1991 | WIPO | |

OTHER PUBLICATIONS

Martin, Richard; "Overcoming DNA Sequencing Artifacts: Stops and Compressions"; Focus 9:1; pp. 8-10.
Martin, Richard; "Overcoming DNA Sequencing Artifacts: G-C Homopolymer Tails"; Focus 9:2; pp. 7-8.
Smith, Lloyd M.; "DNA Sequence Analysis: Past, Present and Future"; (May 1989); pp. 10-25.
Luckey, John A., et al.; "High Speed DNA Sequencing by Capillary Electrophoresis"; Nucleic Acids Research, vol. 18, No. 15, Jun. 15, 1990; pp. 4417-4421.
Drossman, Howard, et al.; "High-Speed Separations of DNA Sequencing Reactions by Capillary Electrophoresis"; Anal. Chem. 1990, pp. 900-903.
Cunningham, Philip R. and James Ofengand; "A Method for the Deterination of Sequence of High G+C% DNA by the Sequential Application of Sequenase and Taq Polymerase"; 714 BioTechniques, vol. 9, No. 6 (1990).

(List continued on next page.)

*Primary Examiner*—John Niebling
*Assistant Examiner*—John S. Starsiak, Jr.
*Attorney, Agent, or Firm*—William H. May; P. R. Harder; Janis C. Henry

[57] ABSTRACT

Disclosed herein are capillary columns for capillary electrophoretic analysis of sample constituents. In an embodiment, the columns comprise a bifunctional layer comprising a positively charged amine group adsorbed to the inner wall of the capillary and an active functional group; a gel composition; hydrophilic polymer; and a separation composition capable of being removed from the column, interspersed within the remainder of the column. The disclosed columns are particularly well suited for the analysis of surfactant: proteinaceous material complexes, nucleic acid sequence, and analysis of restriction fragments according to size.

75 Claims, 8 Drawing Sheets

OTHER PUBLICATIONS

Article —"Sequencing Gel Compressions".

Article from Fourth International Symposium on High Performance Capillary Electrophoresis, Feb. 9–13, 1992, RIA Congress Centre, Amsterdam, p. 69.

Hjerten, Stellan; "High Performance Electrophoresis Elimination of Electroendosmosis and Solute Adsorption"; Journal of Chromatography, 347, pp. 191–198.

Cobb, Kelly A., et al., "Electrophoretic Separations of Proteins in Capillaries with Hydrolytically Stable Surface Structures"; Anal Chem. 1990, vol. 62, No. 22, pp. 2478–2483.

Good, Norman E., et al.; "Hydrogen Ion Buffers for Biological Research"; vol. 5, No. 2, Feb. 1966, pp. 467–477.

Bode, Hans–Joachim; "SDS–Polyethyleneglycol Electrophoresis: A Possible Alternative to SDS–Polyacrylamide Gel Electrophoresis"; FEBS Letters, vol. 65, No. 1 (May 1976), pp. 56–58.

Widhalm, Alexandra, et al.; "Capillary Zone Electrophoresis with a Linear, Non–cross linked Polyacrylamide Gel: Separation of Proteins According to Molecular Mass"; Journal of Chromatography, 549 (1991) pp. 446–451.

Tsuji, Kiyoshi; "High–performance Capillary Electrophoresis or Proteins–Sodium dodecyl sulphate–polyacrylamide gel–filled capillary column for the determination of recombinant biotechnology–derived proteins"; Journal of Chromatography, 550 (1991), pp. 823–830.

Ulfelder, Kathi J., et al.; "Restriction Fragment Length Polymorphism Analysis of ERBB2 Oncogene by Capillary Electrophoresis"; Analytical Biochemistry 200, (1992), pp. 260–267.

CAPILLARY COLUMN CONTAINING REMOVABLE SEPARATION GEL COMPOSITION AND METHOD OF USE

RELATED APPLICATION

This is a continuation-in-part application of pending U.S. Ser. No. 07/829,638, now U.S. Pat. No. 5,213,669 "Capillary Column Continuing a Dynamically Cross-linked Composition and Method of Use", filed on Jan. 31, 1992 by Andras Guttman. This application is related to U.S. Pat. No. 5,098,539, "Gel Containing Microcapillary Columns", issued on Mar. 24, 1992 to Chia-Hui Shieh, and U.S. Ser. No. 07/818/490, filed on Jan. 8, 1992 now abandoned by Kenneth D. Konrad and Stephen L. Pentoney, Jr. for "Capillary Gel" which is a continuation of U.S. Ser. No. 07/649,398, filed on Feb. 1, 1991, now abandoned.

FIELD OF THE INVENTION

The present invention is directed to the analysis of samples in general and in particular to the analysis of sample constituents using capillary electrophoretic techniques. In a preferred embodiment, the invention is directed to a capillary column comprising a bifunctional agent gel composition hydrophilic polymer layer, and removable separation compositions. Preferred embodiments of the removable separation composition include dynamically crosslinked compositions particularly suited for the analysis of, inter alia surfactant:proteinaceous material complexes, denaturing compositions particularly suited for, inter alia sequencing analysis of single and double-stranded nucleic acids, and buffer solutions for the "open tube" analysis of samples.

BACKGROUND OF THE INVENTION

Capillary electrophoresis is one of the most widely used separation techniques in the biologically-related sciences. Capillary electrophoresis is a technique which permits rapid and efficient separations of charged substances. In general, capillary electrophoresis involves introduction of a sample into a capillary tube, and the application of an electric field to the tube. The electric potential of the field both pulls the sample through the tube and separates it into its constituent parts, or separates the components of the sample based upon the relative sizes of those components. An on-line detector can be used to continuously monitor the separation and provide data as to the various constituents. Capillary electrophoresis can be generally separated into two categories based upon the separating medium, these being "open tube" and "gel" capillary electrophoresis.

In "open tube" capillary electrophoresis, the capillary tube is filled with an electrically conductive buffer solution. Upon ionization of the capillary, the negatively charged inner wall will attract a layer of positive ions from the buffer. As these ions flow towards the cathode, under the influence of the electrical potential, the bulk solution (i.e., the buffer solution and the sample being analyzed), must also flow in this direction to maintain electroneutrality. This electroendosmotic flow provides a fixed velocity component which drives both neutral species and ionic species, regardless of charge, towards the cathode. Separations utilizing open tube capillary electrophoresis typically rely upon the charge-to-mass ratios of the constituents traversing the column. I.e., those constituents having a (relative) high charge-to-mass ratio typically transit the column faster than constituents having a lower charge-to-mass ratio.

In "gel" capillary electrophoresis, the capillary is filled with an appropriate separation gel composition. Molecular species such as proteins, peptides, nucleic acids, and oligonucleotides can be separated by causing the species to migrate in a buffer solution under the influence of an electric field. The buffer solution normally is used in conjunction with a low to moderate concentration of the gel composition, such as agarose or polyacrylamide, which functions to minimize the occurrence of mixing of the species being separated. Two primary separating mechanisms exist: a) separations based on differences in the effective charge of the species; and b) separations based on molecular size.

The first of these mechanisms is generally limited to low or moderate molecular weight materials, such as small oligonucleotides (about 1 to about 50 nucleotides in length). This is because there is typically an insignificant difference between the effective charges of high molecular weight materials, making the task of separation difficult or impossible.

Separations based on molecular size are generally referred to as molecular "sieving". Molecular sieving utilizes gel matrices having controlled pore sizes as the separating medium. The separation results from the relative abilities of the different size molecular species to penetrate through the gel matrix; smaller molecules move more quickly than larger molecules through a gel of a given pore size.

Medium-to-high molecular weight oligonucleotides (greater than about 50 nucleotides in length), polypeptides, and proteins are commonly separated by molecular sieving electrophoresis. Proteins comprise both negative charged and positive charged moieties. As such, proteins become charged molecules as they transit a capillary column under the influence of an electric field. Accordingly, in order to separate proteinaceous materials based upon the size of the molecules, these materials must have the same effective charge to mass ratio as they traverse the capillary column.

Achieving the same effective charge to mass ratio is commonly accomplished by treating the proteinaceous materials with a surfactant, such as sodium dodecyl sulphate ("SDS"), and utilizing a polyacrylamide gel material as the sieving medium. Such a procedure is referred to as sodium dodecyl sulphate polyacrylamide gel electrophoresis ("SDS-PAGE"). See, for example, *Gel Electrophoresis of Proteins: A Practiced Approach* (Second Ed). B. D. Harnes & D. Rickwood, Eds. IRL Press, Oxford University Press, 1990. See also, *New Directions in Electrophoretic Methods*, T. W. Jorgenson & M. Phillips, Eds. published by American Chemical Society, Washington, D.C. 1987. Both of these references are incorporated fully herein by reference.

A surfactant, such as SDS, comprises a hydrophobic (water-hating) "tail" and a hydrophilic (water-loving) "head." Thus, a surfactant interacts with a protein species via hydrophobic interactions between the hydrophobic "tail" of the surfactant and the protein species. Upon ionization, the hydrophilic "head" of the surfactant molecules surrounding the protein species become negatively charged, positively charged, or remain neutral; upon ionization, SDS becomes negatively charged. Accordingly, an SDS:protein complex has a uniform charge distribution, and such a complex can then be separated based upon size relative to the pore-size distribution throughout the gel matrix.

Commercially available capillary electrophoresis instruments, such as the P/ACE ™ high performance capillary electrophoresis system (Beckman Instruments, Inc., Fullerton, Calif., U.S.A.), utilize a detection system based upon ultra-violet ("UV") light absorption. While UV detection of SDS-protein complexes in polyacrylamide filled capillaries is possible, such detection is limited to a specific wavelength detection of about 250 nm and higher. This is because of the high UV absorbance associated with both crosslinked and uncrosslinked polyacrylamide gels.

Such detection limitations are a distinct disadvantage particularly with respect to the analysis of proteins. This is because proteins absorb UV light very strongly at 214 nm, due to peptide bonds within proteins. Thus, UV detection of proteins should be conducted at about 214 nm. However, because of the 250 nm and higher detection limitations created by the use of polyacrylamide gels, the sensitivity and selectivity of UV detection of proteinaceous materials using polyacrylamide-based gel systems is limited.

Accordingly, UV detection of surfactant: proteinaceous materials would be greatly improved if on column detection was conducted at lower UV wavelengths. This, in light of the foregoing, requires molecular sieving materials that do not suffer the drawbacks of polyacrylamide gels.

Unlike proteins and peptides, polynucleotides (i.e., macromolecules of deoxyribonucleic acid, DNA, and ribonucleic acid, RNA) have the same charge-to-mass ratio. As such, the analysis of, e.g., DNA, does not typically require utilization of a surfactant as described above. Most typically, the analysis of polynucleotides involves a determination of the sequence thereof, i.e., the determined order of specific nucleic acids along the polynucleotide, or the analysis of restriction fragments, e.g., the analysis, by length, of inherited genetic variations based upon the comparative fragment sizes of polynucleotides subjected to enzymatic cleavage (referred to as "restriction fragment length polymorphisms", or "RFLPs"). Such sequence information provides a wealth of knowledge to research, commercial and medical investigators. RFLPs are utilized, e.g., to correlate the appearance of particular genetic variations with particular polynucleotide fragment lengths.

DNA and RNA are long, threadlike macromolecules, DNA comprising a chain of deoxyribonucleotides, and RNA comprising a chain of ribonucleotides. A nucleotide consists of a nucleoside and one or more phosphate groups; a nucleoside consists of a nitrogenous base linked to a pentose sugar. Typically, the phosphate group is attached to the fifth-carbon ("C-5") hydroxyl group ("OH") of the pentose sugar. Accordingly, such compounds are typically referred to as nucleoside 5'-phosphates or 5'-nucleotides.

In a molecule of DNA, the pentose sugar is deoxyribose, while in a molecule of RNA, the pentose sugar is ribose. The nitrogenous bases in DNA can be adenine ("A"), cytosine ("C"). guanine ("G"), or thymine ("T"). These bases are the same for RNA, except that uracil ("U") replaces thymine. Accordingly, the major nucleotides of DNA, collectively referred to as "deoxynucleotide triphosphates" ("dNTPs"), are as follows: deoxyadenosine 5'-triphosphate ("dATP"); deoxycytidine 5'-triphosphate ("dCTP"); deoxyguanosine 5'-triphosphate ("dGTP"); and deoxythymidine 5'-triphosphate ("dTTP"). The major nucleotides of RNA are as follows: adenosine 5'-triphosphate ("ATP"); cytidine 5'-triphosphate ("CTP"); guanosine 5'-triphosphate ("GTP"); and uridine 5'-triphosphate ("UTP"). By convention, the base sequence of nucleotide chains is written in a 5' to 3' direction, i e , 5'-ATCG-3', or simply ATCG.

Two complementary single chains (or "strands") of nucleotides, held together by (relatively) weak hydrogen bonds between the nucleotides, form a complete double-stranded DNA or RNA macromolecule. The specificity of binding between the bases is such that A always binds to T (or U in the case of RNA), and C always bonds with G. Thus, for the sequence 5'-ATCG-3', the sequence 3'-TAGC-5' will lie immediately across therefrom. Because of this specificity in binding, the sequence of a single-stranded template of DNA or RNA can be determined by determining the bases which bind to the template. This, in essence, is the basis for nucleotide sequencing.

Another unique and useful form of NTPs exist. These are referred to as chain terminating dideoxynucleotide triphosphates, or "ddNTPs." ddNTPs differ from dNTPS in that they lack a 3'-hydroxyl group. Accordingly, while ddNTPs can be incorporated into the growing primer strand via the 5'-triphosphate portion thereof, the absence of a 3'-hydroxyl group prevents formation of a phosphodiester bond with a succeeding dNTP (or ddNTP). Accordingly, once a ddNTP is incorporated into the primer strand, further extension of that strand is not possible.

DNA sequencing protocols, particularly those suited for automated DNA sequencing instrumentation formats, principally rely upon the methodology developed by Sanger et al., *Proc. Natl. Acad. Sci. USA* 74:5463–5467 (1977) (hereinafter, "Sanger et al."). Generally, the Sanger et al. protocol involves four separate syntheses, whereby a single stranded template (i.e., the sequence to be determined which can be obtained via, e.g., denaturation of double-stranded DNA or cloning of the DNA template into, e.g., bacteriophage M13 vector), is provided with a primer (i.e., a short oligonucleotide complementary to a portion of the template) such that elongation of the primer proceeds via DNA polymerase (an enzyme that brings about the incorporation of a dNTP or ddNTP along the growing primer strand). Each reaction is terminated (via the appropriate ddNTP utilized in that reaction) at one of the four bases, i.e., A, T, C, or G, via the incorporation of the appropriate chain terminating agent. Thus, if the templates have the sequence 5'-XXXATGCTGCA-3' and the primer is complementary to XXX, the addition of dGTP, dCTP, dTTP, dATP and ddATP, as well as DNA polymerase, would lead to the formation of two primer-extension fragments: 5'-XXXTA-3' and 5'-XXXTACGA-3', which are complementary to the template. In a second synthesis, the protocol would be the same, except that, e.g., ddTTP would be utilized instead of ddATP, leading to the formation of 5'-XXXT-3' and 5'-XXXTACGACGT-3'. The third synthesis would utilize ddCTP (5'-XXXTAC-3' and 5'-XXXTACGAC-3'), and the fourth would utilize ddGTP (5'-XXXTACG-3' and 5'-XXXTACGACG-3'). By utilizing labelled ddNTPs, dNTPs or primer, and subjecting the various extension products to gel electrophoresis, various discrete bands will be obtained on the resulting gel, due to the various electrophoretic mobilities of the extension fragments. From these bands, one can determine the sequence of the extension fragments, such that the sequence of the template is readily determined therefrom.

While polynucleotides have the same charge-to-mass ratio, single stranded polynucleotides, necessary for sequencing reactions, suffer from the possibility of secondary structure formation, i.e., the folding of the single strand via internal base-pairing of complementary bases along the single strand. Thus, the sequencing gel typically incorporates a denaturing material therein, i.e., a material that reduces or prevents such secondary structure formation.

As can be appreciated from the foregoing, different separating materials can be utilized for different protocols. Typically, however, this requires the use of different capillary columns for each protocol. This is because such separating materials (other than the buffers used in open tube capillary electrophoresis) can become substantially "fixed" within the column. Thus, it has, heretofore, been impractical to attempt to remove the separation material from the column for any reason such that each time a new material is required for separating samples, an entirely new column must be obtained or prepared. Such columns are typically expensive, the preparation thereof is tedious and time consuming, and replacement thereof requires the shut-down of the capillary electrophoretic instrument, thus decreasing throughput and increasing the time for analysis.

What are needed, then, are capillary columns useful in the analysis of a variety of materials, and which are compatible with different separating materials, such that a separating material used for sample analysis can be removed from the column, and a different separating material can be added thereto, without affecting the performance of the column or any coatings utilized therewith.

SUMMARY OF THE INVENTION

Disclosed herein are capillary columns containing separation compositions which are applicable to the capillary electrophoretic analysis of, e.g., surfactant:-proteinaceous material complexes and single-stranded and double-stranded polynucleotides. In an embodiment, the invention is directed to capillary columns comprising a capillary column having an interior cavity defined by a wall with an inner surface; a bifunctional agent adsorbed to the inner surface of the wall; a gel composition copolymerized with the bifunctional agent; a hydrophilic polymer adsorbed into the gel composition; and a separation composition filling substantially the remainder of the capillary column. Exemplary separation compositions are dynamically crosslinked compositions, denaturing compositions and open tube buffer solutions. Most preferably, the bifunctional agent comprises at least one positively charged amine and at least one active functional group; the gel composition is acrylamide crosslinked with bisacrylamide; the hydrophilic polymer is 10% dextran; the dynamically crosslinked composition is used for the analysis of proteins and peptides and comprises between about 0.01% and about 1.5% polyethylene oxide, between about 0.0% and less than about 2.00% polyethylene glycol, between about 0.0% and about 2.0% of a surfactant, between about 0.0% and about 99.0% of a polyol, and between about 0.0M and 1.0M of a pH buffer, where the pH of the composition is between about 2.0 and about 10.0; the denaturing composition is used for determination of the sequence of polynucleic acids and comprises 20% dextran (MW: 2,000,000), 7M urea, and tris-hydroxymethyl amino methane-borate buffer, pH 8.3; and the open tube buffer solution is used for the analysis of proteinaceous materials and has an ionic strength and pH appropriate for the sample to be analyzed.

BRIEF DESCRIPTION OF THE DRAWINGS

The following drawings are presented for the purpose of reference in conjunction with the Detailed Description of Preferred Embodiments of the Invention.

DETAILED DESCRIPTION OF PREFERRED EMBODIMENTS

Figure 1:
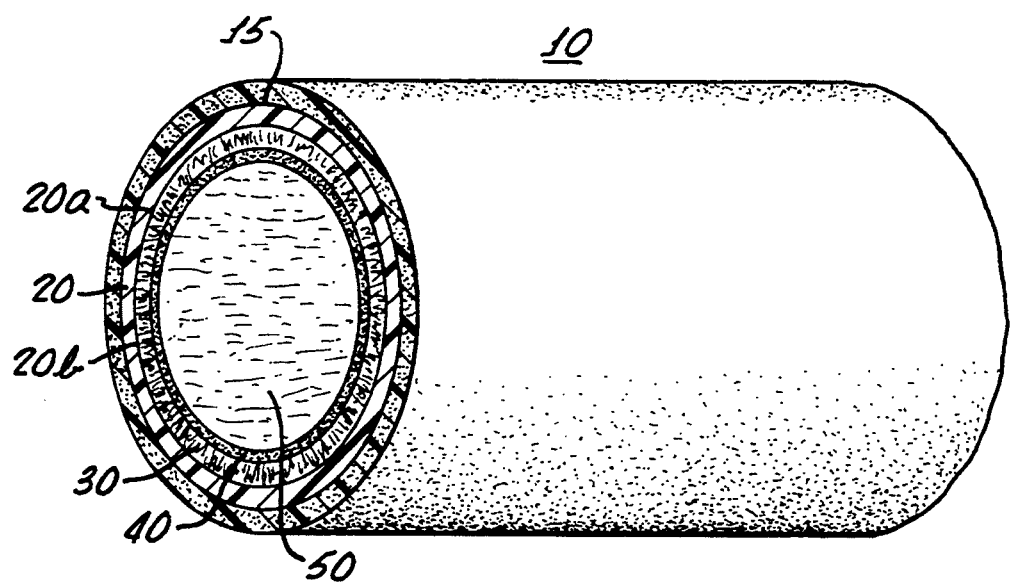
FIG. 1 provides a magnified prospective view of the end of a capillary column comprising a bifunctional agent, a polymeric gel, a hydrophilic polymer layer, and a separation composition in accordance with the present invention.

Disclosed herein are capillary columns comprising combinations of the following: (1) bifunctional agent which is adsorbed to the inner wall of the capillary column; (2) gel composition copolymerized with the bifunctional agent; (3) hydrophilic polymer adsorbed onto the polyacrylamide gel; and (4) separation composition substantially interspersed throughout the remainder of the column.

As used herein, the term "capillary column" means a capillary comprising an interior cavity defined by a wall with an inner surface, where the internal diameter range of the capillary is between about 2 $\mu$m and 2000 $\mu$m and most preferably between about 100 $\mu$m and about 200 $\mu$m. If the detection system of the capillary electrophoretic system is based upon UV absorbance, then the capillary is preferably made of a UV transparent material, such as, for example, glass or fused silica, with fused silica being most preferred. If the detection system of the capillary electrophoretic system is based upon e.g. radioactive detection or fluorescence detection, then the capillary is preferably made of a material conducive to such systems. Alumina, beryllium, TEFLON TM -coated materials, glass and fused silica are exemplary materials. The capillary column should be capable of withstanding a wide range of applied electrophoretic fields of between about 10 volts per centimeter ("V/cm"), up to about 1000 V/cm. The capillary column may be coated on the outside (using, e.g., a polyamide material) for ease of handling.

As used herein, the term "combinations" is meant to indicate that one or more of the following components are included within the capillary column: bifunctional agent; gel composition; hydrophilic polymer. Thus, while it is preferred that all three components are utilized, this is not an absolute. For example, with respect to the denaturing composition, such composition can be utilized singularly with bifunctional agent adsorbed to the inner wall of a capillary column.

In accordance with the U.S. Pat. No. 5,098,531 (which is incorporated herein by reference), a "bifunctional agent" is an agent adsorbed to the inner surface of a capillary wall and comprises at least one positively charged amine and at least one active functional group. A particularly preferred embodiment of a bifunctional agent has the following chemical structure:

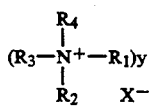

where three of $R_1$, $R_2$, $R_3$, and $R_4$ can be independently selected from the group consisting of:

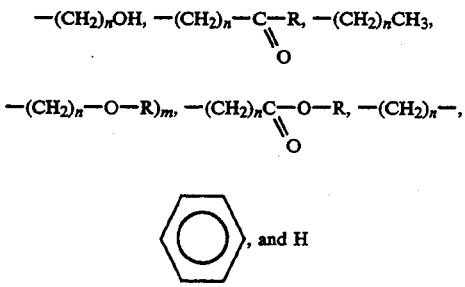

where
n is an integer between 0 and 10;
m is an integer between 0 and 5:
R is selected from the group consisting of:

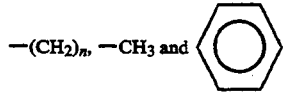

the proviso being that at least one of $R_1$, $R_2$, $R_3$, and $R_4$ must comprise an active functional group comprising a moiety selected from the group consisting of:

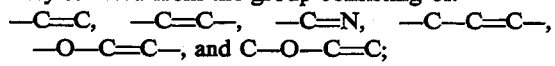

y is an integer between 1 and 5000, more preferably between 1 and 2000, and most preferably 1; and
X is selected from the group consisting of fluorine, chlorine, bromine, iodine and astatine.

In a particularly preferred embodiment, $R_1$, $R_2$, and $R_3$ are each $-(CH_2)_n-CH_3$, where n is 0 (i.e., "$CH_3$"), $R_4$ is $-CH_2CH=CH_2$, X is iodine, and y is 1. Accordingly, a particular preferred embodiment of the bifunctional agent can be represented as follows:

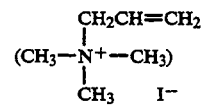

referred to as "trimethyl allyl ammonium iodide" or "TAAI" bifunctional agent. The functional group portion of the coating is capable of copolymerizing with a gel solution.

Preferably, the "gel solution" is a polymeric gel comprising at least one monomer and at least one cross-linking agent which has a pore structure which can be adjusted by varying the amounts of monomer and cross-linking agents, as well as the reaction conditions. Preferred polymeric gel materials are based on the monomer arcylamide and the cross-linking agent N-N'-methylenebis-acrylamide; other monomer and cross-linking agents applicable in the production of capillary electrophoric gels are well known and varied and will not be discussed herein in detail. Other materials, such as, e.g., a catalyst, may also be included in the solution.

The pore size of polyacrylamide gels is dependent on total monomer concentration (%T) and on the concentration of cross-linker (%C). Pore size can be progressively increased by reducing %T at a fixed %C; however, very dilute gels are mechanically unstable and pore sizes greater than 80 nm cannot be obtained. An alternative approach is to progressively increase %C at a fixed %T and %C can be derived as follows:

$$\% T = \frac{\text{grams acrylamide} \times \text{grams bisacrylamide}}{100 \text{ ml solvent}}$$

$$\% C = \frac{\text{grams of bisacrylamide} \times 100}{\text{grams of bisacrylamide} \times \text{grams of acrylamide}}$$

see, Hjerten, *Chromographic Reviews* 5,9: 122-2319 (1967), which is incorporated herein by reference. Preferably, %T is from about 1 to about 30, more preferedly from 3 to about 15, and most preferedly about 3. Preferedly %C is from about 0 to about 15, more preferedly from about 0.01 to about 6, and most preferedly about 0.2.

As used herein, a "hydrophilic polymer" is a polymer which does not physically interact with a surfactant material and/or proteinaceous materials and is capable of being chemically or physically attached to a gel composition by, e.g., free radical or van der Wall force interactions, respectively. Exemplary hydrophilic polymers include, but are not limited to, dextran, polyethylene glycol, polyethylene oxide, cellulose derivatives, polyvinyl alcohol, agarose, and modifications or mixtures thereof. The concentration of any of the hydrophilic polymers preferably range from about 0.1% to about 40%, more preferedly about 5% and about 20%, and most preferedly about 10%. The upper range can be determined by the highest soluble concentration for any of he hydrophilic polymers. Most preferedly, 10% dextran is utilized as the hydrophilic polymer.

As used herein, the phrase "separation composition" is a composition capable of being placed into a capillary column and substantially removed from the column, and which can be utilized for the analysis of samples via capillary electrophoretic techniques. The term "analysis" is intended to encompass a variety of techniques, such as physical separation of the constituent parts of a sample, one from the other; determination of the constituent parts of a sample based upon, e.g., calibration curves and the like; determination of the order of the constituent parts of the sample as in, for example, DNA sequencing; separation of the constituent parts of a sample based upon size or length as in, for example, RFLPs. Stated again, any "separation composition" useful in the capillary electrophoretic analysis of a sample which can be placed into and substantially removed from the disclosed columns is intended to fall within the broad definition of "separation composition". Exemplary separation compositions are dynamically crosslinked compositions, denaturing compositions and open tube buffer solutions.

As used herein, the phrase "dynamically crosslinked composition" means a gel-like solution having a three-dimensional network of polymer chains held together by hydrogen bonding and dispersed in a liquid phase. The dynamically crosslinked composition is a viscous liquid having a sufficient structure for a degree of rigidity which allows for, inter alia, molecular sieving based upon the size of the materials to be separated.

In a particularly preferred embodiment, the dynamically crosslinked composition comprises about 1.0% PEO; about 1.0% PEG; about 1.0ethylene glycol, about 0.1% of the same surfactant used in the formation of the surfactant:proteinaceous material complex; and 100 mM of a pH buffer, where the composition has a pH of between about 8.0 and about 9.0, and a viscosity of less than about 500 centipoise. When the composition does not include PEG, it is a linear, as opposed to crosslinked, composition. PEG is preferably added to the composition to dynamically cross-link the PEO. Accordingly, "dynamically crosslinked composition," as that phrase is used herein, includes linear compositions such as compositions not including PEG as described above.

As used herein, a "polyol" is a composition comprising repeating "CHOH" moieties; an exemplary polyol is ethylene glycol. The intent of the polyol is to "circulate" throughout the dynamically cross-linked composition such that any portion(s) of the inner wall of the capillary which may not be "coated" with any of the bifunctional agent, gel composition, and/or hydrophilic polymer, is "coated" by the polyol.

As used herein, the term "surfactant" is a substance having hydrophobic and hydrophilic properties, and exhibiting either a negative charge, a positive charge or neutral charge upon ionization. The hydrophobic portion of the surfactant is capable of interacting with a proteinaceous material via hydrophobic interactions such that the material is surrounded by the hydrophilic portion of the surfactant. Representative anionic surfactants include, for example, sodium-dodecyl sulphate ("SDS"), decyl-sulphate, and deoxycholate. Representative cationic surfactants include, for example cetyl-trimethylammonium bromide ("CTAB") and cetylpyridinium chloride ("CPC"). Representative nonionic surfactants include, for example, polyoxyethylene ethers such as Triton X 100 ™ and Triton DF-16 ™, and polyoxyethylenesorbitans such as BRIJ-35 ™, the TWEEN ™ surfactants, and LUBROL W ™. All of the foregoing trademark-designated surfactants are available from Sigma Chemical Co., St Louis, Mo. Of the surfactants, anionic surfactants are preferred when used in conjunction with untreated fused silica columns. Most preferably, the surfactant is the anionic surfactant SDS.

As used herein, the term "proteinaceous material" means, proteins (both natural and those derived via recombinant nucleic acid technology), peptides, polypeptide, nucleic acids and oligonucleotides. It is to be understood that while the disclosed dynamically crosslinked composition finds particular applicability in the analysis of proteinaceous materials, and in particular proteins, the disclosure is not limited to such materials. Thus, the disclosed dynamically crosslinked composition can be utilized for the analysis of other materials capable of being analyzed by capillary electrophoretic techniques. Because proteinaceous materials as defined herein can be charged upon ionization, it is to be understood that the dynamically crosslinked composition need not incorporate a surfactant therein. For example, deoxyribonucleic acid molecules have the same charge-to-mass ratio; therefore, a surfactant is not required to achieve this result. However, it is preferred that the composition include a surfactant for the analysis of proteinaceous materials.

As used herein, the term "denaturing composition" means any composition that can be utilized for analyzing nucleic acids by means of capillary electrophoretic protocols, and in particular, nucleic acid sequencing and analysis of RFLPs. Although definitionally distinct, denaturing compositions may fall within the defined parameters of dynamically cross-linked compositions, and vice-versa. Exemplary denaturing compositions comprise: (a) from between about 7% to the solubility limit of at least one of the aforementioned hydrophilic polymers, preferably from between 15% to about 50% of the aforementioned hydrophilic polymers, and more preferably about 20% of the aforementioned hydrophilic polymers; (b) at least one denaturant capable of preventing or substantially reducing the occurrence of secondary structures, e.g., between about 6M and about 8M urea, between about 3M and between 8M urea in conjunction with between about 20% and about 40% (by volume) of non-urea denaturing agent, and up to about 98% of non-urea denaturing agent, the non-urea denaturing agent comprising at least one moiety capable of disrupting hydrogen bonding and at least one moiety capable of reducing intramolecular base pairing; (c) and at least one buffer capable of maintaining the current through the denaturing composition between about 5 and about 60 $\mu$A ("micro-ampers") under an applied electric potential of between about 100 and about 1000 V/cm. Preferably, the viscosity of the denaturing solution is greater than about 3,000 centipoise, and more preferably greater than or equal to about 4,000 centipoise. In a particularly preferred embodiment, the denaturing composition comprises 7M urea, 20% dextran (weight/volume; MW: 2,000,000), and 0.1M tris/.25M boric acid buffer pH 8.3

Most preferably, the hydrophilic polymer is 20% dextran. When dextran is utilized, it is preferred that the molecular weight thereof is greater than about 750,000, more preferably greater than about 1,500,000, and most preferably, greater than or equal to about 2,000,000. For the hydrophilic polymers, the concentration thereof can decrease as the molecular weight thereof increases; thus, for any given hydrophilic polymer, as the molecular weight thereof increases, a lower concentration can be utilized.

Most preferably, the denaturant is 7M urea. Preferably, the non-urea denaturing agents which can be utilized singularly or in combination with urea and amides:

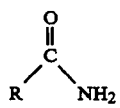

where the NH₂ moiety preferably functions to disrupt hydrogen bonding, and R, which is selected from the group consisting of hydrogen, an alkyl chain having from 1 to about 6 carbon atoms, benzene ring, and substituted benzene rings, preferably functions to reduce or prevent intramolecular base paring. A preferred R is hydrogen such that a preferred non-urea denaturing agent is formamide. It is preferred that about 35% non-urea denaturing agent be used in conjunction with 7M urea.

The buffer portion of the denaturing composition is selected principally with respect to the current passing through the composition. For example, if the composition is too resistive, i.e. the current is low, the sequencing resolution will be deleteriously impacted; if the current is too high, the resulting heat displaced throughout the composition will negatively impact the nucleic acids. At room temperature, the current through the composition is preferably between about 5–30 μA, most preferably about 10 μA. If the current is less than a preferred value, the ionic strength of the buffer should be increased, and if the current is greater than a preferred value, the ionic strength of the buffer should be decreased. Increasing the ionic strength of the buffer can be accomplished by the addition of a salt, e.g., sodium chloride to the buffer, while decreasing the ionic strength can be accomplished by diluting the buffer (but preferably not the denaturing composition in toto). Because current through the composition can be readily determined, and because those skilled in the art can readily and efficiently optimize the ionic strength of the buffer, it is considered within the skill of the art to efficiently select an appropriate buffer combination.

As used herein, the term "open tube buffer solution" is intended a broad definition that encompasses any buffer solution which can be used in the capillary electrophoretic analysis of samples. Stated again, any buffer solution which can be utilized in the open tube capillary electrophoretic analysis of samples (whether or not the inner wall of the capillary column is treated or coated), is intended to fall within the scope of this definition. Such buffer solutions are well known and varied based upon the investigative needs of the artisan; accordingly, the skilled artisan can readily select an appropriate buffer solution that is particularly suited for a given sample to be analyzed. For example, the ionic strength of the open tube buffer solution is preferably less than about 200 mM; however, because the column is coated, the ionic strength can be higher than 200 mM, i.e., as high as about 1000 mM. However, as the ionic strength increases, Joule heating also increases such that the sample can be negatively affected by the heat. When high ionic strength buffers are utilized, it is preferred that the internal diameter of the column be less than about 50 μm, preferably less than about 25 μm, such that the Joule heating can be dissipated. The pH of the open tube buffer solution is preferably selected with respect to the sample to be analyzed and can range from about 2.0 to about 12.0. Typically, for the analysis of proteins, the pH is between about 6.0 and about 8.0 in order to avoid denaturation of the protein. Those skilled in the art can readily select appropriate open tube separation buffers that are most efficient for the sample being investigated.

As used herein, the terms "remove", "removable", and "removing" in relationship to the separating composition means that the capillary column can be regenerated by forcing the separating composition out of the column (leaving the bifunctional agent-gel solution-hydrophilic polymer layer substantially in tact) and refilling the column with separating composition. Thus, a single capillary can be utilized for many analytical runs whereby only the separating composition need be removed and replaced. Any protocol for removing the separation composition can be utilized; preferably, when the capillary column is utilized in conjunction with commercially available capillary electrophoresis instruments having a pressure-injection feature for sample introduction, the composition is removed via pressure applied to the composition—i.e., the composition is "pushed" or "blown" from the column, using, e.g., gas or liquid as the means for removing the composition from the columns.

As used herein, the terms "regenerate" and "regenerated" in relationship to the capillary column means that a column comprising combinations of bifunctional agent-polymer gel-hydrophilic polymer and a separating composition can be subjected to techniques which can remove the separating composition such that the capillary can be substantially refilled with a different portion of the same separating composition, or with an entirely different separating composition.

When the detection system of the capillary electrophoretic system is based upon UV absorbance, the pH buffer and the buffers used in conjunction with, e.g., the hydrophilic polymer, dynamically cross-linked composition, the denaturing composition, and open tube buffer solution are preferably UV transparent. The term "UV transparent" as used herein, means having negligible absorbance throughout the UV wavelength range of between about 195 nm and about 350 nm. Exemplary UV transparent buffers include, for example, the so-called "Good" buffers (see Good, N. E. et al "Hydrogen Ion Buffers for Biological Research" *Biochemistry* 5/2: 467–477 (1966) which is incorporated herein by reference). The Good buffers can be described as being zwitterionic buffers covering the range of $pK_a$ from 6.15 to 8.75, and include 2-(N-morpholine) ethanesulfonic acid ("MES"), N-(2-acetamide) iminodiacetic acid ("ADA"), piperazine-N,N'-bis(2-ethanesulfonic acid ("PIPES"), n-(2-acetamide)-2-aminoethanesulfonic acid ("ACES"), (2-aminoethyl) trimethyl-ammonium chloride hydrochloride ("Cholamine") , N,N-bis(2-hydroxy-ethyl)-2-aminoethane sulfonic acid ("TES"), N-2-hydroxy-ethylpiperazine-N'-2-ethanesulfonic acid ("HEPES"), tris-hydroxymethyl amino methane ("TRIS"), N-tris(hydroxyl-methyl)methylglycine ("Tricine"), N,N-bis(2-hydroxyethyl)-glycine ("Bicine"), 2-(N-cyclohexylamino) ethane-sulfonic acid ("CHES"), and mixtures of the foregoing. A particularly preferred pH buffer for UV detection purposes is TRIS-CHES.

While the foregoing buffers are preferred for use in conjunction with UV detection, it is to be understood that such buffers can also be utilized with, e.g., radioactive detection or fluorescent detection instruments. Additionally, when UV detection is not utilized, buffers that include constituents having aromatic rings or peptide bonds can be utilized as the pH buffer. TRIS-histidine is an example of such a buffer.

The pH of the buffer used in conjunction with the dynamically cross-linked composition is principally selected with respect to the type of surfactant utilized. For cationic surfactants, the pH of the buffer should be in the acidic range (i.e. between about 2.0 and 5.0); for anionic surfactants, the pH of the buffer should be in the alkaline range (i.e. between about 8.0 and 10.0); for nonionic surfactants, the pH of the buffer is between about 5.0 and about 8.0. With respect to the preferred SDS surfactant, a most preferred pH is about 8.8. The pH of the buffers used in conjunction with denaturing compositions is preferably between about 7 and about 9, more preferably between about 8.0 and about 8.5, and most preferably about 8.3. The pH of the open tube buffer solutions are primarily selected based upon the sample to be analyzed; accordingly, the pH thereof can be between about 2.0 and about 12.0.

Capillary electrophoresis using separation compositions disclosed above includes the steps of introducing an aliquot of a sample containing constituents to be separated into the column of the invention, applying an electric field of at least about 10 V/cm to the column, allowing a current of between about 1.0 to about 100 $\mu$A to pass through the column, and detecting the constituents of the sample as they migrate past an on-line detector. Introduction of the samples can be accomplished by the electrokinetic injection method or pressure injection. The electric field may be a continuous or pulsed electric field; those skilled in the art will appreciate the distinction between these types of fields. Preferably, a continuous electric field is utilized. "Capillary electrophoresis" as used herein is broadly defined and is intended to include protocols where the separation and analysis of samples is accomplished by subjecting a capillary column comprising the sample to an applied electric field. Capillary electrophoresis thus includes isoelectric focusing and isotachophoresis.

The capillary "running buffer" is dependent principally on the detection system. For UV detection, the running buffer should be UV transparent. Preferably, the running buffer is the same buffer utilized in conjunction with the separating composition. When the separating composition does not include a pH buffer, the running buffer is selected based upon the detection system, as indicated above. Accordingly, the pH buffers disclosed above can be utilized for the running buffer. With respect to denaturing compositions, the running buffer is preferably the same as the denaturing composition. For example, when the denaturing composition comprises 7M urea, 20% dextran, and trisborate buffer, the running buffer comprises substantially the same components.

The analysis of proteinaceous materials can be made at UV wavelengths of 214 nm using the disclosed dynamically cross-linked composition. This is a distinct advantage over polyacrylamide gels. Additionally, the disclosed dynamically crosslinked polymer can be used for quantitative analysis of, e.g., proteinaceous materials over large molecular weight ranges. As those in the art appreciate, such calibration plots for polyacrylamide gels is quite difficult to achieve, thus heretofore making quantative analysis evasive.

With respect to the analysis of DNA, the disclosed columns comprising denaturing compositions can be utilized for sequencing without the need to replace the entire column after a series of sequencing runs; rather, the denaturing gel can be replaced while the column remains in place on the instrument. For UV detection systems, analysis is preferably conducted at wavelengths of 260 nm.

With respect to open tube analysis of samples, the disclosed columns are particularly well suited in analytical situations where it is desirable to eliminate or reduce electroosmotic flow through the capillary column.

The following examples are presented for illustrative purposes only and are not intended, nor should they be construed to be, a limitation on the foregoing disclosure or the claims to follow.

EXAMPLES

Example I

Instrumentation

A. Capillary Electrophoresis (UV Detection)

Capillary electrophoresis of samples described in the following Examples was performed on a Beckman Instruments, Inc. PACE TM high performance capillary electrophoresis system. This system contains built-in 200, 214, 254, 260, 280 and 415 nm narrow-band filters for on-line detection. The detection window was located approximately 7.0 cm from the column outlet and 40 cm from the column inlet. For SDS-protein analysis, detection was at 214 nm; for DNA analysis, detection was at 260 nm.

Samples were placed on the inlet tray of the above-referenced capillary electrophoresis system. Samples were automatically injected into the dynamically cross-linked composition by utilizing the pressure injection mode for 1–90 seconds. Samples where injected into the denaturing composition by electrokinetic injection, using 10 kV for 10 sec.

Capillary columns had a column length of 47 cm, an effective column length of 40 cm, and an internal diameter of 100 $\mu$m. For analysis of SDS-proteins, electric field strength was 300 V/cm (14.1 kV for 47 cm); current utilized was 25–30 $\mu$A. For analysis of DNA, electric field strength was 320 V/cm (15 kV for 47 $\mu$m); current utilized was between 10–12 $\mu$A.

B. Capillary Electrophoresis (Laser-Induced Fluorescence)

Sequencing of DNA was accomplished using a High Performance Capillary Electrophoresis/Laser Induced Fluorescence ("HPCE/LIF") instrumentation format. For the HPCE/LIF format, a 2 mm length of the protective polyamide coating was removed from the surface of the fused silica capillary (200 $\mu$m i.e.) using a thermal wire stripper (Western Electric Products Co., San Clemente, Calif. Model G) equipped with blade elements. This section of the capillary was supported between two compression fittings. The ends of the separation capillary were dipped in 5 ml vials containing approximately 4.7 ml of a running buffer solution (comprising the same components s the denaturing composition). Connection to a high voltage power supply (for example, a Bertan Associates, Inc., Model 205A-30R power supply) was provided by paliney wires submersed in each of the buffer reservoirs. The high voltage power supply was operated in the negative polarity configuration with the outlet end of the capillary maintained at ground potential. The current passing through the denaturing composition was measured as a potential drop across a 1-K$\Omega$ resistor placed in the ground side of the circuit. The system was enclosed in a plexiglass container for precautionary purposes. The temperature of the separation capillary was maintained at room temperature.

Sample introduction into the instrument was accomplished by inserting the inlet end of two separation capillaries into microfuge tubes containing the sample mixture, and a short strip of paliney wire for electrical contact to high voltage. High voltage (i.e., between about 5–50 kV) was applied for about 10–15 sec.

Detection of the labelled −20 primer was accomplished by laser induced fluorescence. BODIPY TM-derivative labelled primers (infra), were utilized with excitation at 543.5 nm and detection at 580 nm, using a helium-neon laser. Fluorescent emission was collected and directed through two interference filters (Barr Associates, Westford, Mass., product no. Custom 5 Cavity; 550 nm, or 580 nm, 10 nm band pass) and onto the photocathode of an end-on photomultiplier tube ("PMT") (Hamamatsu, San Jose, Calif. product no. R2228).

Example II

Material Preparation

A. Preparation of Bifunctional Agent 106 g of sodium carbonate (J. T. Baker, Phillipsburg, N.J., Cat. No. 3604), 37.5 ml of alkyl amine (Aldrich Chemical, Milwaukee, Wis., Cat. No. 24107-5), and 200 ml of methanol (B&J, McGaw Park, Ill., Cat. No. 230) were stirred in a 1L round bottom flask. 124.5 ml of iodomethane (Aldrich, Cat. No. 1-778-0) in 50 ml of ethanol was slowly added to the flask by a dropping funnel. The reaction mixture was stirred overnight (18) hours. The methanol was evaporated on a rotavap. 15 ml of iodomethane was then added to the flask, followed by 10 minutes of shaking. 200 ml of water and 20 ml of tetrahydrofuran (B&J, Cat. No. 340) was added to the solution and stirred for 20 minutes. The sodium carbonate was then filtered, and the aqueous layer was collected and filtered through a 0.2 micron membrane filter.

The resulting solution included the bifunctional agent trimethyl allyl ammonium iodide.

B. Preparation of Bifunctional Agent: Polyacrylamide-Hydrophilic Polymer Columns Capillary columns were first rinsed with 1N HCl for 15 minutes, followed by 1N NaOH for 15 minutes, followed by deionized water for 15 minutes as a pretreatment step. Thereafter, the trimethyl allyl ammonium iodide bifunctional agent of Example 1A was placed into the pretreated column and was maintained there for 30 minutes.

Following adsorptional the bifunctional agent to the inner wall of the pretreated column, a polyacrylamide coating was added thereto. The polyacrylamide coating was prepared by dissolving and degassing 0.06 g of ultrapure acrylamide (ICN. Irvine, Calif. Cat. No. 814320) and 0.00012 g of biscarylamide (ICN. Product No. 800173) in 2 ml of deionized water (percent-by-volume: acrylamide—3%; bisacarylamide—0.2%). This solution was filtered through a 0.2 micron nylon filter. To the acrylamide solution was added 10 μl of a 10% N,N, N',N'-tetramethylenediamine (BRL, Gaithesburg, Md. Cat. No. 5524), and 10% ammonium persulfate (BRL, Cat. No. 5523), and this solution was pushed into the column using 5 psi helium gas; the pressure was gradually reduced to 0 over a 3 min. period. After an additional 2 min., the capillary ends were capped with a silicon plug and stored at room temperature for 45 minutes. Thereafter, the polyacrylamide gel was pushed from the column by water under nitrogen gas pressure at 60 psi, leaving a layer of polyacrylamide gel and to the adsorbed bifunctional agent.

This was followed by the addition of a hydrophilic layer to the polyacrylamide. To 2 ml of 100 mM of TRIS-CHES buffer (pH 8.8) was added 0.2 g of dextran (Sigma Chemical Co., St. Louis, Mo., Product No. D-1390 MW 70,000) for a dextran concentration (weight/volume) of 10%. To this was added 40 μl of 10% cerium sulfate tetrahydrate (Fluka, Switzerland, Product No. 22440) in deionized water. This solution was then quickly pushed into the capillary using 20 psi helium gas; after 10 min., the pressure was gradually reduced to 0 psi. The column was then end-capped with silica plugs and stored at room temperature for 24 hrs.

C. Dynamically Crosslinked Composition 10 g of PEO (MW 900,000; Aldrich Chemical Co., Milwaukee, Wis., Product No. 18,945-6) and 10 g PEG (mw 35,000; Fluka, Ronkonkoma, N.Y., Product No. 81310) were mixed with 10 ml ethylene glycol (VWR, Product No. EM-EX0564-1) and 50 ml deionized water for 10 min. in a 1.2 liter wide-neck flask. Thereafter, 700 ml of deionized water was added thereto, followed by stirring with a magnetic bar at 50° C. for three hours. After this, 200 ml of Running Buffer was added thereto, followed by stirring for one hour. 10 ml of 10% SDS (1.0 g SDS completely dissolved in 10 ml deionized water) was then added, followed by addition of deionized water to achieve a final volume of 1000 ml, and overnight stirring at room temperature. Prior to use, the dynamically crosslinked composition was sonicated for 5 min. to remove air bubbles.

The viscosity of the dynamically crosslinked composition was determined using an ELV-8 TM viscometer, Col-Parmer, Inc., Chicago, Ill., using 100 ml of the composition. Viscosity was determined to be 150 centipoise at 25° C. relative to equal volumes of distilled water (20 centipoise) and glycerol (1100 centipoise) measured at the same temperature.

D. Preparation of Denaturing Composition 242 g of ultra pure tris-hydroxy methyl amino urethane (ICN, Schwartz-Mann, Irvine, Calif., Product No. 819620) and 3.09 g of boric acid (ICN, Schartz-Mann, Product No. 195074) were combined and 135 ml of double deionized water was added thereto, followed by stirring; this provided a 0.1M tris/.25M boric acid solution. Thereafter, 84.08 g of ultra pure urea (ICN, Schartz-Mann, Product No. 821527) was slowly added thereto under constant stirring; this resulted in a solution comprising 7M urea. Prior to use, the solution was filtered through a 0.2 micron filter and degassed. The pH of the solution was 8.3. In order to achieve a 20% (weight/volume) of dextran, to 8.0 g dextran (Sigma Chemical Corp., St. Louis, Mo.) Product No. D-5376; MW-2,000,000) was added a sufficient amount of the aforementioned solution to derive a total volume of 40 ml.

The viscosity of the denaturing composition was determined using the ELV-8 TM viscometer, using 100 ml of the composition. Viscosity was determined to be 4300 centipoise at 25° C. relative to 2% methyl cellulose (measured value was 1800 centipoise; stated viscosity for methyl cellulose is 4000 centipoise).

E. Preparation of Bifunctional Agent: Polyacrylamide-Hydrophilic Polymer-Separation Composition Columns and Process for Regenerating the Columns Prior to addition of the separation compositions of Examples 1C and 1D to the column of Example 1B, the column was rinsed with 0.5 ml of 1N HCL. The dynamically crosslinked composition was added to the column via pressure injection using about 1 psi helium. The denaturing composition was added to the column via pressure injection using about 30 psi using helium.

Because the bifunctional agent is presumptively adsorbed to the column via ionic forces; the polymer gel is crosslinked to the bifunctional agent; and the hydrophilic polymer is adsorbed to the polymer gel, these components are intended to be "permanently" affixed to the inner wall of the capillary column. The separation compositions, on the other hand, are not intended to be "permanently" affixed to the hydrophilic polymer. Accordingly, these compositions can be removed from the column such that the column can be regenerated. Thus, rather than having to replace the entire column after a series of analytical runs, an investigator can remove the separation composition from the column and regenerate that same column using another separation composition.

For the dynamically cross-linked composition, such removal was accomplished using between 10-20 psi helium, followed by rinsing for 2 min. using 1N HCl. Thereafter, the dynamically crosslinked composition was added to the column in the manner set forth above. A similar protocol was used to remove the denaturing composition from the column, except that the column was refilled directly in the instrument using the denaturing composition.

Reference is made to FIG. 1 for a schematic representation of the layers of the capillary column and prepared in Examples 1A-E, where a capillary column 10 comprising an activated inner wall 15. Physically adsorbed to the inner wall 15 is bifunctional agent 20 comprising a positively charged amino compound or amino polymer 20a and an active functional group 20b; active functional group 20b is copolymerized with polymeric gel 30 and hydrophilic polymer 40 is adsorbed onto polymeric gel 30. Substantially interspersed throughout the remainder of the column is separation composition 50.

F. Preparation of Bifunctional Agent-Denaturing Composition Column

A capillary column was coated with the bifunctional agent of Example 1A and the denaturing composition of Example 1D was interspersed throughout the remainder of the interior of the column using about 30 psi of helium.

G. Running Buffer Solutions

A 0.5M TRIS-CHES buffer (pH 8.8) was prepared by dissolving 12.1 g TRIS (ICN Biochemicals, Irvine, Calif.; Product No. 819620) in 100 ml deionized water. Solid CHES (ICN, Product No. 101434) was added with continuous stirring until a pH of 8.8 was achieved. A final volume of 200 ml was achieved using deionized water.

The running buffer for columns comprising the denaturing composition was 7M 20% dextran, 7M urea, 0.1 M tris/0.25 borate, pH 8.3.

H. Model Protein Sample Preparation

A 0.3M TRIS sample buffer was adjusted with 1:1 HCl to pH 6.6, followed by addition of 10% SDS thereto, as follows. 36.3 g TRIS was dissolved in 500 ml deionized water, followed by addition of 1:1 diluted HCl (VWR, San Francisco, Calif., Product No. VW3110-3) with continuous stirring and pH monitoring until a pH of 6.6 was achieved. 100 g SDS (ICN, Product No. 811034) was added with continuous stirring and a final volume of 1000 ml was achieved using deionized water.

Model Protein SDS-protein standards (Sigma Chemical Corp., St. Louis, Mo., Product No. MW-SDS-200) comprised a lyophilized mixture of six proteins having a molecular weight range of from between 29,000 to about 205,000:

1) Carbonic anhydrase: MW—29,000
2) Ovalbumin: MW—45,000
3) Bovine Serum Albumin: MW—66,000
4) Phosphorylase B: MW—97,000
5) $\beta$-Galactosidase: MW—116,000
6) Myosin: MW—205,000

Figure 2:
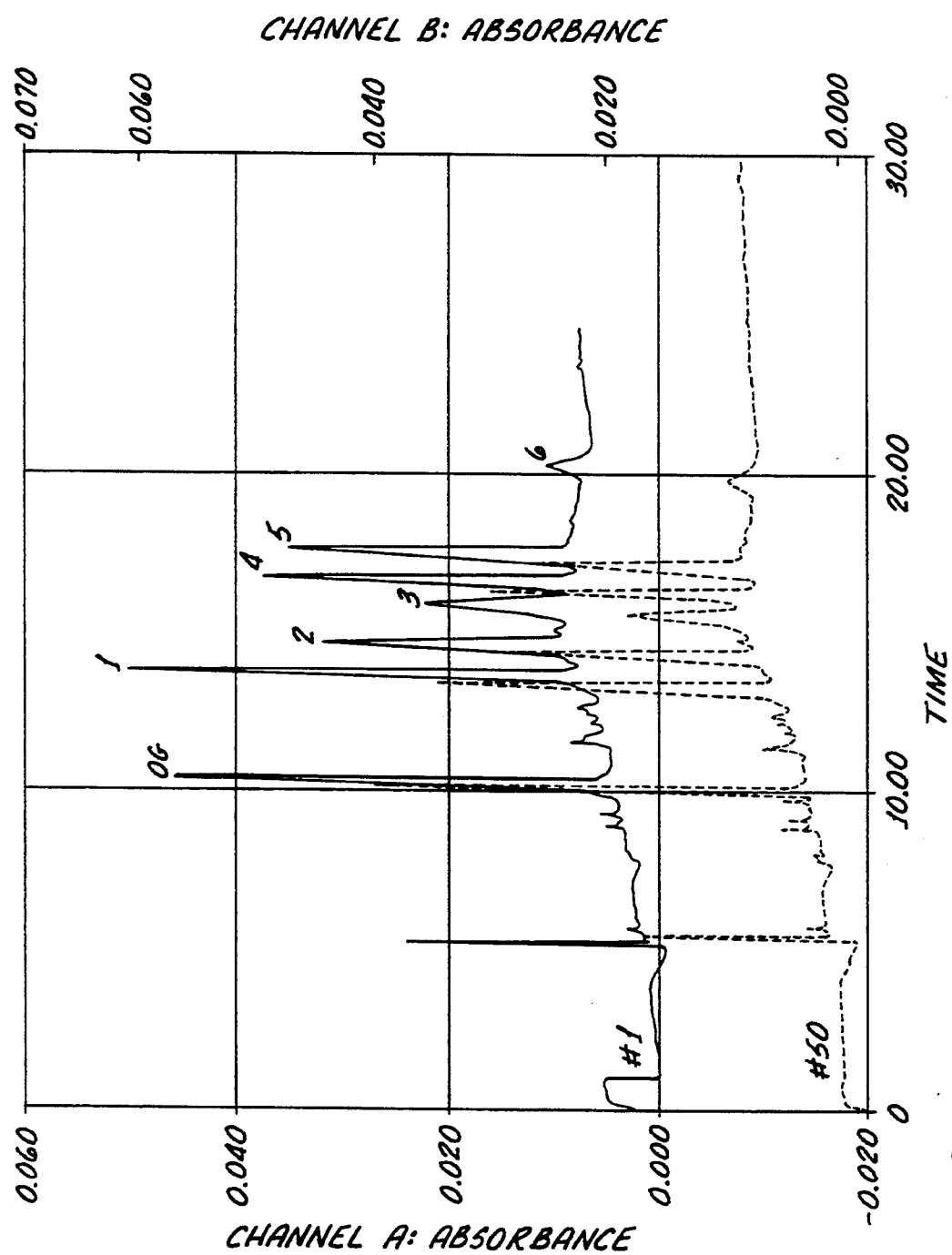
FIG. 2 are superimposed electropherograms of the 1st and the 50th separations of 29,000 to 205,000 molecular weight SDS-protein standard mixture using a 1.0% PEO/1.0% PEG/1.0% ethylene glycol dynamically crosslinked composition, layered onto 10% dextran adsorbed into polyacrylamide copolymerized to a quarternary alkyl amine bifunctional agent.
Figure 3:
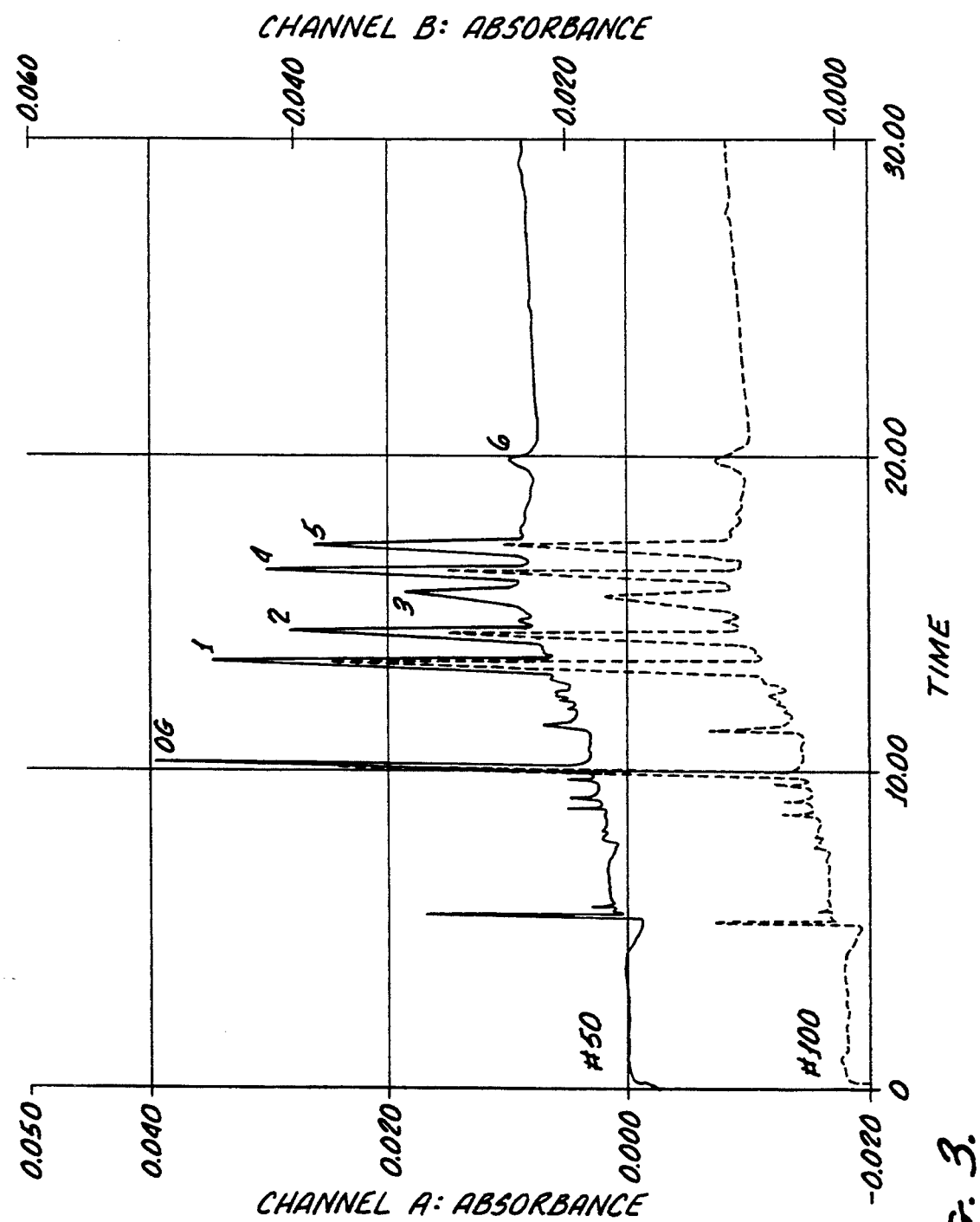
FIG. 3 are superimposed electropherograms of the 50th and 100th separations of the standard mixture of FIG. 2 using the materials of FIG. 2.
Figure 4:
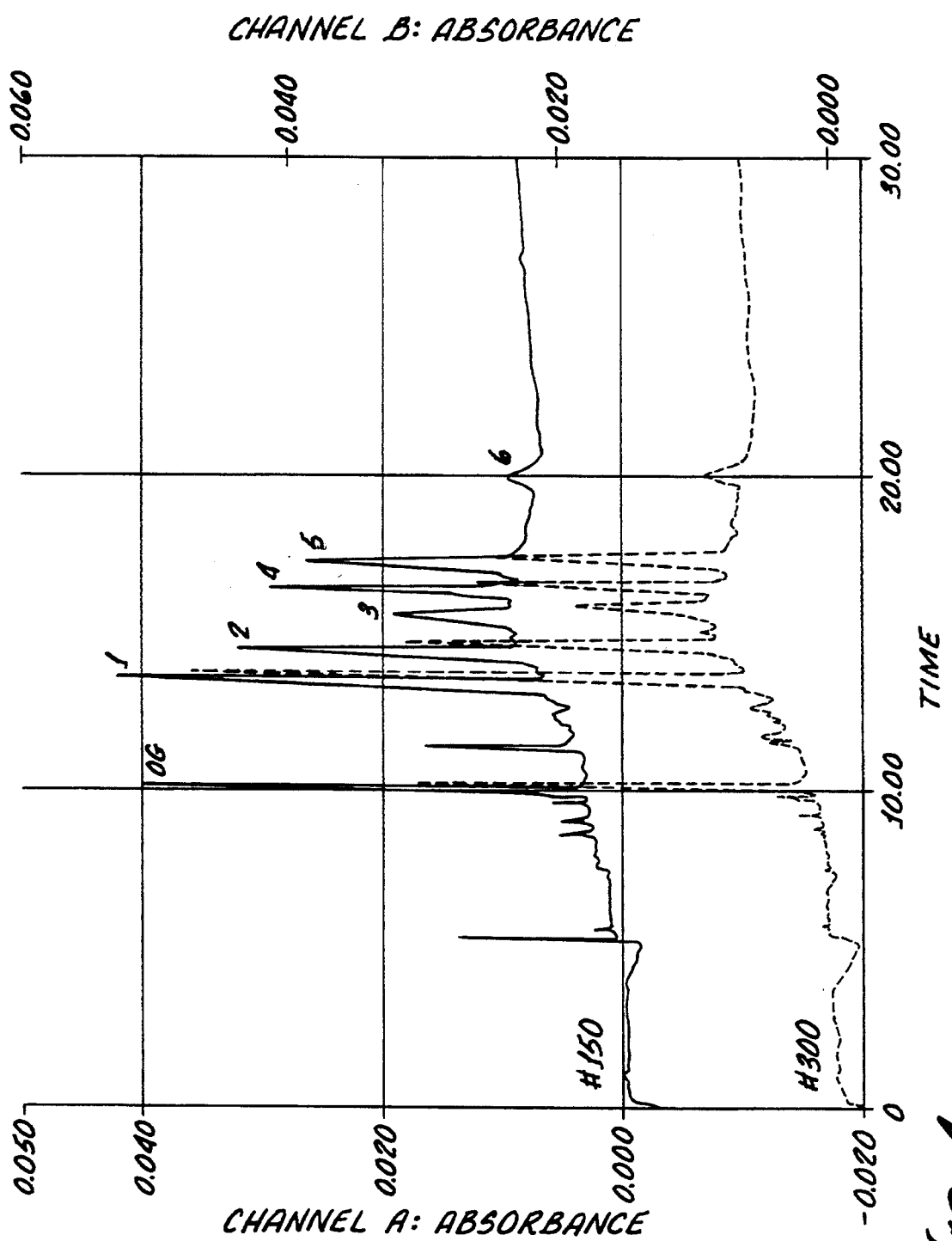
FIG. 4 are superimposed electropherograms of the 150th and 300th separations of the standard mixture of FIG. 2 using the materials of FIG. 2.

(The numerical designators correspond to the numbered peaks on FIGS. 2-4). Orange G ™ ("O.G.") dye (7-hydroxy-8-phenylazo-1,3-napthalenedisulfonic acid; Sigma, Product No. 03756) was utilized as an internal standard. A 0.1% solution, in deionized water, was utilized for the Examples.

Protein disulfide linkages were broken using 2-mercaptoethanol (ICN, Product No. 190242). As those skilled in the art appreciate, in the presence of a surfactant and a reducing agent, most multichain proteins will bind the surfactant to a constant value and the disulfide bonds will be broken by the reducing agent. Thus, the secondary structure of the protein will be lost and the surfactant-protein complex is assumed to adopt a random coil confirmation. Accordingly, proteins treated in this manner have a uniform shape and identical mass to charge ratios. Thus, it should be appreciated that any reducing agent is applicable, such as, for example, dithiothreitol, (DTT) and mercaptoethanol.

Samples were prepared by admixing 0.1 to 0.2 mg of the Model Proteins. 40 $\mu$l of the sample buffer; 10 $\mu$l of the Orange G solution; and 5 $\mu$l of 2-mercaptoethanol. A final solution volume of 125 $\mu$l was achieved using deionized water. This final mixture was boiled in a water bath (100° C.) for 15 min. in a closed microcentrifuge vial, then cooled on ice water for 2 min. before introduction into the capillary column.

I. Sequencing Reaction Protocol

DNA sequencing reactions were performed using primers labelled with a BODIPY ™ -derivative having an excitation wavelength of 543 nm and an emission wavelength of 580 nm (proprietary to Molecular Probes, Inc., Eugene, Oreg. 1 $\mu$g of M13mp18 DNA (Pharmacia, Piscataway, N.J., product no. 27-1516-01) was mixed with 0.5 picomole of the aforementioned primer and 2 $\mu$l of 5X reaction buffer (USB, Cleveland, Ohio, Sequenase ™ polymerase kit, product no. 70775) in a total volume of 10 $\mu$l. This solution was heated to 65° C., allowed to cool to 37° C., and 1 $\mu$l of DTT solution and 1 $\mu$l of Mn++buffer (from the aforementioned Sequenase ™ kit) were then added thereto. Thereafter, 9 $\mu$l of a prewarmed termination mix was added thereto, followed by the addition of 1—2 $\mu$l of undiluted Sequenase ™ polymerase. The termination mix was comprised of concentration ratio mixture of 100 parts of one dNTP to 1 part of three of the four ddNTPs. Accordingly, the termination mix was comprised of (a) 2880 $\mu$M total dNTPs (500 $\mu$M of each of the four dNTPs), and (b) 7.2 $\mu$M of three of the four ddNTPs in a ratio of 3.6 $\mu$m ddATp:2.7 $\mu$m ddATp:0.90 $\mu$m ddCTp:0 $\mu$m ddTTp (4:3:1:0). The reaction was incubated for 30 min. at 37° C. after which it was placed on ice, followed by the addition of 2 $\mu$l of 3.0M sodium acetate, followed by 60 μl of ice-cold ethanol. The DNA was pelleted by centrifugation at 12,000 RPM for 15 min. and rinsed once with 70% ethanol. The pellet was then dried and resuspended in 2.0 μl of 80% formamide, 10 mM EDTA. The sample (which can be stored at −20° C. in the dark until analyzed) was heated at 95° C. for 1 min. just prior to injection onto the capillaries.

Example III

Separation of Model SDS-Proteins

For the analysis of the Model SDS-Proteins, a 60 nl aliquot thereof was analyzed using the column of Example IIB comprising the dynamically cross-linked composition of Example IIC. After each analysis, the column was regenerated and replaced with different portions of the same composition without removal of the column from the instrument.

FIG. 2 provides electrophorogram results and the 1st and 50th analytical runs, i.e. a 60 nl aliquot of the sample was analyzed, and the column was regenerated fifty times, when the analysis of the 50th aliquot (60 nl) was obtained. As is evident, excellent resolution of the Model SDS-Proteins was efficiently and rapidly obtained in about 20 min. It is additionally observed that the relative locations of the peaks are nearly the same for the 1st and the 50th runs; this indicates, inter alia, that the bifunctional agent-gel composition-hydrophilic layer remained substantially intact over the fifty column regenerations, in that if the material had substantially dissolved, the possibility for differing endosmotic flow, sample adsorption, etc. would have increased which would have led to differing analytical results.

FIG. 3 provides electrophorograms of the 50th and 100th analytical runs of the Model SDS-proteins using the regeneration protocol described above; these runs performed as described above. Excellent resolution was efficiently and rapidly obtained without deleterious impact upon the "permanent" components of the capillary. These same types of results are evidenced with the 150th and 300th analytical runs (FIG. 5).

Example IV

Single Base Resolution of Nucleic Acids

For the analysis of poly $dA_{40-60}$ using the UV detection capillary electrophoretic system, the column of Example IIB comprising the denaturing composition of Example IIC were utilized. As those in the art appreciate, a sample of poly $dA_{40-60}$ comprises a mixture of poly deoxyadenosines comprising from 40 to 60 deoxyadenosine nucleosides. Accordingly, for example, all of the poly $dA_{45}$, based upon their identical lengths, would be expected to traverse the column in a substantially unitary fashion such that these are detected "together". As such, the difference in lengths between $dA_{45}$ and $dA_{46}$ should be resolved as defined and separate peaks.

Figure 5A:
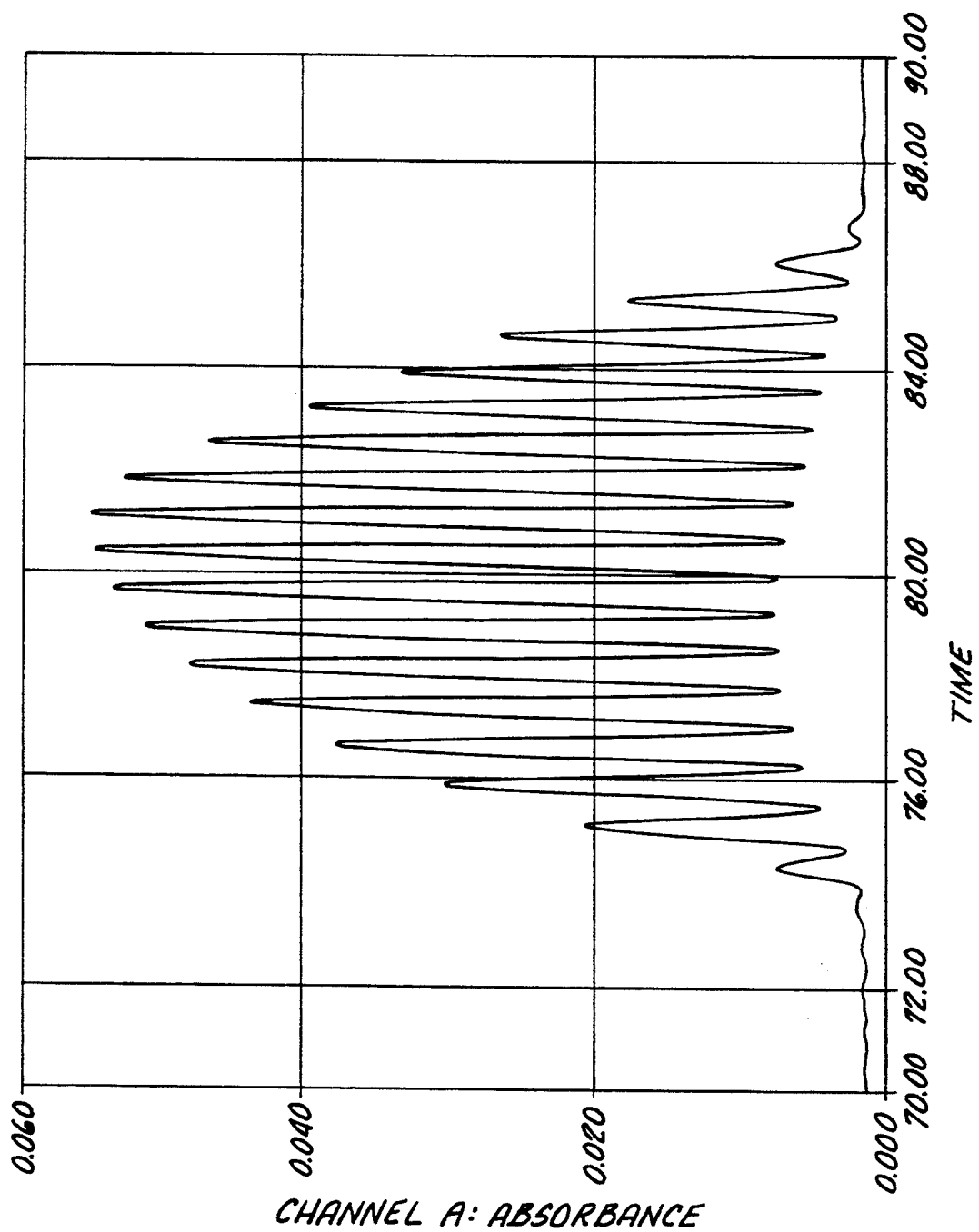
FIGS. 5A and 5B are an electropherogram results evidencing the single base resolution of poly $dA_{40-60}$ using 20% dextran (NEW: 2,000,000), 7M urea, tris-borate buffer, pH 8.3, with a regeneration of the column between each analysis.
Figure 5B:
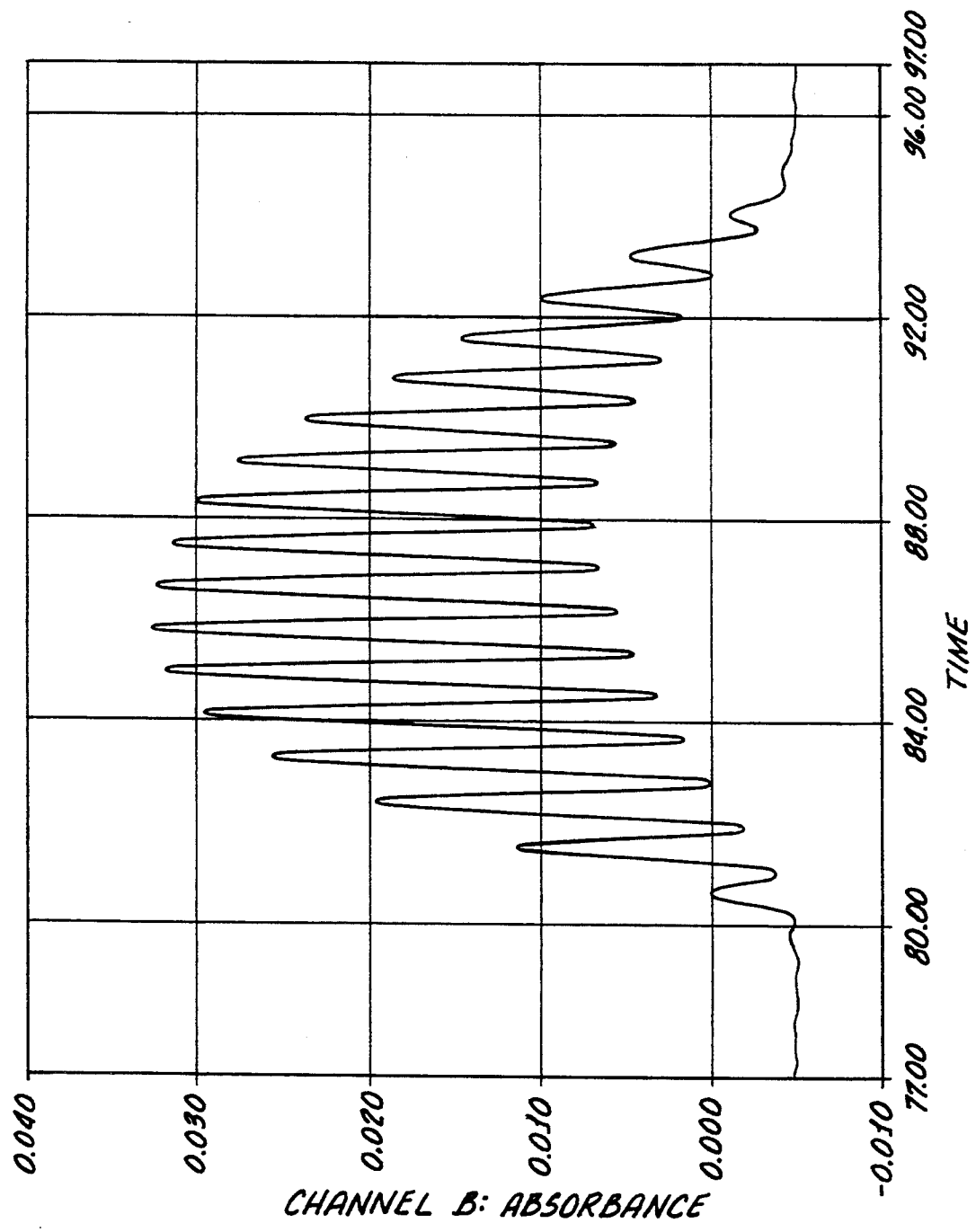

FIGS. 5A and 5B evidence such resolution. FIG. 5A provides electropherogram results of the first analytical run of 1–50 D units $A_{260}$/ml aliquot of poly $dA_{40-60}$ (Pharmacia, Uppsola, Sweden, Product No. 27-7988-01); thereafter, the column was regenerated with a different portion of the denaturing composition, without removing the column from the instrument, and a second aliquot (150 D units $A_{260}$/ml) of poly $dA_{40-60}$ was analyzed. These results are set forth in the electropherogram of FIG. 5B.

Example V

Sequencing Analysis of Polynucleotide

Using a ddNTP ratio of 4ddATP:3ddGTP:1ddCTP:0ddTTP, peaks of various heights proportional to the ratios were utilized for the HPCE/LIF. Sequencing of positions 8 to 32 of the template MP13mp18 was accomplished; this portion of the sequence is as follows:

5′-ATG-CCT-GCA-GGT-CGA-CTC-TAG-AGG-A-3′

As such, fragments terminated by ddATP are proportionally "higher" on the electrophorogram than fragments terminated by ddGTP, etc.

Figure 6:
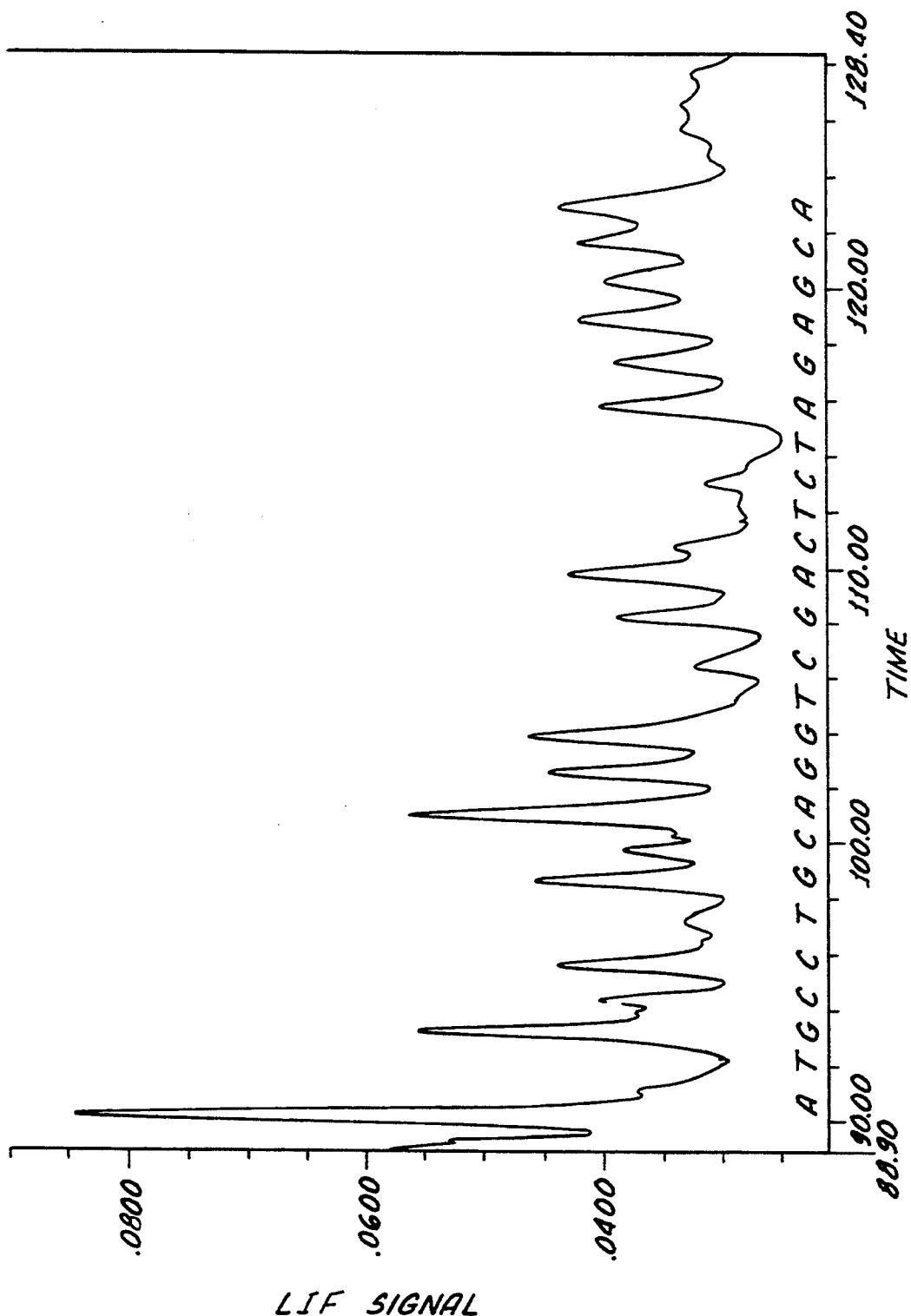
FIG. 6 is an electropherogram result evidencing single base resolution sequencing analysis of a segment of the template M13mp18 comprising position 8 to position 33, using the separation composition of FIG. 5, in a column comprising bifunctional agent.

Two conditions were examined. In the first, the column of Example IIA was utilized in conjunction with the denaturing composition of Example IID, and in the second, the column of Example IIB was utilized in conjunction with the same denaturing composition as in the first condition. These analyses were conducted simultaneously using a double-column analytical format. FIG. 6 provides electropherogram results of the designated sequence are derived from the bifunctional agent-denaturing-composition (first condition), and FIG. 7 provides electropherogram results of the designated sequence as derived from the bifunctional agent-gel composition-hydrophilic polymer-denaturing composition (second condition).

Figure 7:
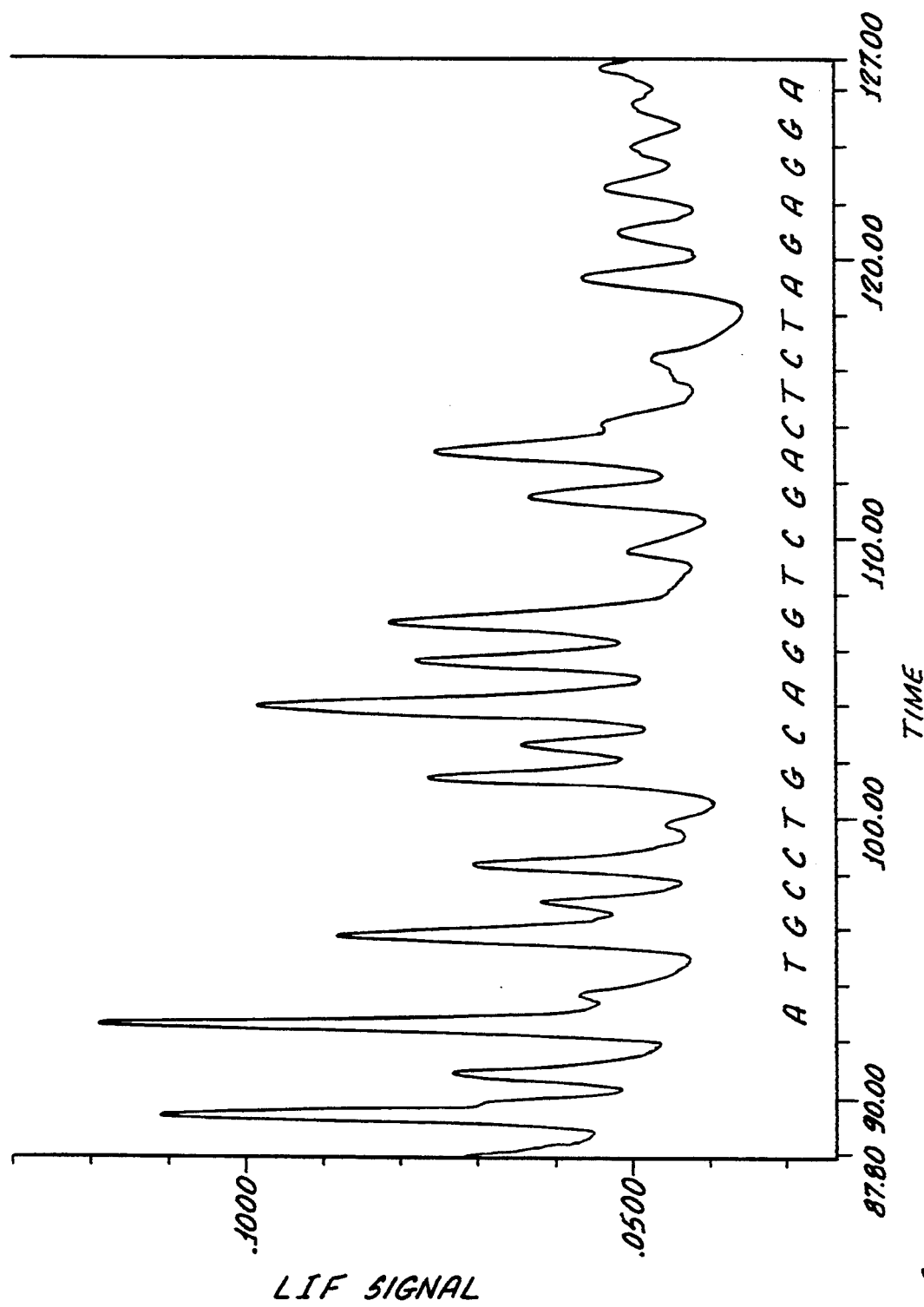
FIG. 7 is an electropherogram result evidencing single base resolution sequencing analysis of the M13mp18 section of FIG. 6 using the separation composition of FIG. 5, in a column comprising bifunctional agent-gel composition-hydrophilic polymer.

FIGS. 6 and 7 evidence, inter alia, that the disclosed invention can be utilized for the sequencing of polynucleotides.

While the foregoing has been described in considerable detail, it is to be understood that the embodiments disclosed in the Detail Description and Examples are not to be construed as limiting the disclosure or the claims to follow. The invention is not limited to automated instruments; for example, the dynamically cross-linked compositions and denaturing compositions are applicable to so-called "slab-gel" electrophoresis modifications and changes that are within the purview of those skilled in the art are intended to fall within the scope of the following claims.

What is claimed is:

1. A capillary column comprising:
   a) a capillary column having an interior cavity defined by a wall with an inner surface;
   b) at least one bifunctional agent adsorbed to the inner surface of the wall, said agent comprising at least one positively charged amine and at least one active functional group;
   c) at least one gel composition bound to the active functional group of said agent;
   d) at least one hydrophilic polymer bound to the gel composition; and
   e) at least one separation composition interspersed through the remainder of said interior cavity, said separation composition capable of being removed from said column.

2. The capillary of claim 1 wherein the active functional group of said agent comprises at least one carbon atom attached to a second atom by a double bond.

3. The capillary of claim 1 wherein the active functional group of said agent comprises at least one carbon atom attached to a second atom by a triple bond.

4. The capillary of claim 1 wherein the bifunctional agent is represented by the following structure:

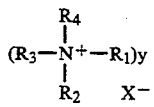

$R_1$, $R_2$, and $R_3$ are each selected independently from the group consisting of

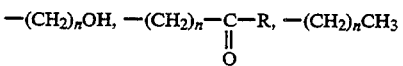

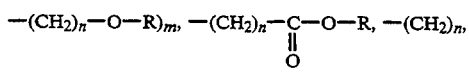

, and H where
n is an integer between 0 and 10,
m is an integer between 0 and 5,
R is selected from the group consisting of

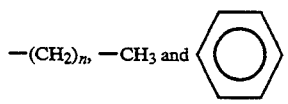

and
$R_4$ is an active functional group;
y is an integer between 1 and 5000, and
X is selected from the group consisting of fluorine, chlorine, bromine, iodine and astatine.

5. The capillary of claim 4 wherein $R_1$, $R_2$, and $R_3$ of said agent are each —$(CH_2)_nCH_3$.

6. The capillary of claim 5 wherein n is 0.

7. The capillary of claim 4 wherein the active functional group of said agent comprises a moiety selected from the group consisting of 8. The capillary for claim 4 wherein the active functional group of said agent comprises a —C=C— moiety.

9. The capillary of claim 4 wherein y is an integer between 1 and 2000.

10. The capillary of claim 4 wherein y is 1.

11. The capillary of claim 4 wherein X is iodine.

12. The capillary of claim 1 wherein the bifunctional agent is represented by the following structure:

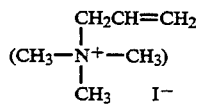

13. The capillary of claim 1 wherein the gel composition comprises a copolymer of acrylamide and at least one cross-linking agent.

14. The capillary column of claim 1 wherein the active functional group is copolymerized with the gel composition.

15. The capillary column of claim 1 wherein said hydrophilic polymer is selected from the group consisting of dextran, polyethylene glycol, polyethylene oxide, cellulose derivatives, polyvinyl alcohol, agarose, and modifications or mixtures thereof.

16. The capillary column of claim 1 wherein the concentration of said hydrophilic polymer is from about 0.1 to about 40%.

17. The capillary column of claim 1 wherein the concentrating of said hydrophilic polymer is from about 5% to about 20%.

18. The capillary column of claim 9 wherein the concentration of said hydrophilic polymer is about 10%.

19. The capillary column of claim 1 wherein said hydrophilic polymer is dextran present in a concentration of about 10%.

20. The capillary column of claim 1 wherein said separation composition is selected from the group consisting of dynamically cross-linked composition, denaturing composition and open tube buffer composition.

21. The capillary column of claim 20 wherein said separation composition is a dynamically crosslinked composition comprising:
   i) between about 0.01% and about 1.5% polyethylene oxide ("PEO");
   ii) between about 0.0% and less than about 2.0% polyethylene glycol ("PEG");
   iii) between about 0.0% and about 2.0% of a surfactant;
   iv) between about 0.0% and about 99% of a polyol; and
   v) between about 0.0M and about 1.0M of a pH buffer, where the composition has a pH of between about 2.0 and about 10.0, and the viscosity of the composition is less than about 4,000 centipoise.

22. The capillary column of claim 21 wherein said composition comprises about 1.0% polyethylene oxide.

23. The capillary column of claim 21 wherein said composition comprises about 1.0% polyethylene glycol.

24. The capillary column of claim 21 wherein the polol is about 1.0% ethylene glycol.

25. The capillary column of claim 21 wherein said surfactant is selected from the group consisting of sodium-dodecyl sulphate, decyl-sulphate, polyoxyethylene ethers, polyoxyethylenesorbitans, deoxycholate, cetyltrimethylammonium bromide and cetylpyridinium chloride.

26. The capillary column of claim 21 wherein said surfactant is sodium dodecyl sulphate.

27. The capillary column of claim 26 wherein said composition comprises about 0.1% sodium dodecyl sulphate.

28. The capillary column of claim 21 wherein said pH buffer is ultra-violet light transparent.

29. The capillary column of claim 28 wherein said pH buffer comprises zwitterionic buffers.

30. The capillary column of claim 28 wherein said pH buffer is selected from the group consisting of 2-(N-morpholine) ethanesulfonic acid, N-(2-acetamide) iminodiacetic acid, piperazine-N,N'-bis(2-ethanesulfonic acid, N-(2-acetamide)-2-aminoethanesulfonic acid, (2-aminoethyl) trimethyl-ammonium chloride hydrochloride, N,N-bis(2-hydroxy-ethyl)-2-aminoethane sulfonic acid, N-2-hydroxy-ethylpiperazine-N'-2-ethanesulfonic acid, tris-hydroxymethyl amino methane, N-tris(hydroxylmethyl)methylglycine, N,N-bis(2-hydroxyethyl)-glycine, 2-(N-cyclohexylamino) ethane-sulfonic acid and mixtures of the foregoing.

31. The capillary column of claim 28 wherein said pH buffer is a TRIS-CHES buffer.

32. The capillary column of claim 31 wherein the molarity of said buffer is 100 mM.

33. The capillary column of claim 21 wherein the pH of said composition is between about 8.0 and about 9.0.

34. The capillary column of claim 20 wherein said separation composition is a dynamically crosslinked composition comprising:
 a) about 1.0% polyethylene oxide;
 b) about 1.0% polyethylene glycol;
 c) about 1.0% sodium dodecyl sulfate; and
 d) about 1.0% ethylene glycol;
where the pH of the composition is between about 8.0 and about 9.0 and the viscosity of the composition is less than about 500 centipoise.

35. The capillary column of claim 20 wherein said composition is a denaturing composition.

36. The capillary column of claim 35 wherein said denaturing composition comprises:
 i) from about 7% to the solubility limit of at least one hydrophilic polymer;
 ii) at least one denaturant;
 iii) at least one buffer.

37. The capillary column of claim 36 wherein said hydrophilic polymer is selected from the group consisting of dextran, polyethylene glycol, polyethylene oxide, cellulose derivatives, polyvinyl alcohol agarose, modifications of the foregoing, and mixtures of the foregoing.

38. The capillary column of claim 37 wherein the concentration of said hydrophilic polymers is between about 15% to about 50%.

39. The capillary column of claim 37 wherein the concentration of said hydrophilic polymer is about 20%.

40. The capillary column of claim 39 wherein said hydrophilic polymer is dextran having a molecular weight of at least about 750,000.

41. The capillary column of claim 36 wherein said denaturant is selected from the group consisting of
 i) 6M to about 8M urea;
 ii) a combination of between about 3M and about 8M urea and between about 20% and about 40% of a non-urea denaturing agent; and
 iii) up to about 98% of a non-urea denaturing agent.

42. The capillary column of claim 36 wherein said denaturant is 7M urea.

43. The capillary column of claim 41 wherein the non-urea denaturing is represented by the following structure:

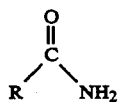

wherein R is selected from the group consisting of hydrogen, an alkyl chain having from 1 to about 6 carbon atoms, benzene ring and substituted benzene rings.

44. The capillary column of claim 43 when R is hydrogen.

45. The capillary column of claim 36 wherein the buffer has a pH of between about 7.0 and about 9.0.

46. The capillary column of claim 36 wherein the buffer has a pH of between about 8.0 and about 8.5.

47. The capillary column of claim 36 wherein the buffer has a pH of about 8.3.

48. The capillary column of claim 47 wherein the buffer is tris-hydroxymethyl amino-methane borate.

49. The capillary column of claim 35 wherein said denaturing composition comprises about 7M urea, about 20% dextran having a molecular weight of at least about 750,000, and a buffer having a pH of between about 8.0 and about 9.0.

50. The capillary column of claim 20 wherein said separation composition is an open tube buffer composition.

51. A method of performing capillary electrophoresis comprising:
 a) introducing an aliquot of a sample containing constituents to be separated into a capillary column comprising:
  1) a capillary column having an interior cavity defined by a wall with an inner surface;
  2) at least one bifunctional agent adsorbed to the inner surface of the wall, said agent comprising at least one positively charged amine and at least one active functional group;
  3) at least one gel composition bound to the active functional group of said agent;
  4) at least one hydrophilic polymer bound to the gel composition; and
  5) at least one separation composition capable of being removed from said column.
 b) applying an electric field of at least about 10 volts per centimeter to the capillary column;
 c) separating the sample into its constituent parts; and
 d) detecting the constituents of the sample.

52. The method of claim 51 wherein the sample is selected from the group consisting of:
 i) surfactant-protein complexes; and
 ii) polynucleotides.

53. The method of claim 51 wherein said detecting is selecting from the group consisting of UV spectrophotometry, radioactive detecting of fluorescence detecting.

54. The method of claim 51 wherein the microcapillary is selected from the group consisting of glass, alumina, beryllia, fused silica and TEFLON.

55. The method of claim 51 wherein the capillary is fused silica.

56. The method of claim 51 wherein said separation composition is selected from the group consisting of dynamically cross-linked compositions; denaturing compositions; and open tube buffer compositions.

57. The method of claim 51 wherein said separation composition is a dynamically cross-linked composition.

58. The method of claim 57 wherein said dynamically crosslinked composition comprises:
 a) about 1.0% polyethylene oxide;
 b) about 1.0% polyethylene glycol
 c) about 0.1% sodium dodecyl sulfate; and
 d) about 1.0% ethylene glycol;
where the pH of the composition is between about 8.0 and about 9.0 and the viscosity of the composition is less than about 500 centipoise.

59. The method of claim 56 wherein the separation composition is a denaturing composition.

60. The method of claim 59 wherein the denaturing composition comprises 20% dextran, 7M urea, and a buffer, wherein the pH of said composition is between about 8.0 and about 9.0.

61. The method of claim 56 wherein the separation composition is an open tube buffer composition.

62. A denaturing composition useful for the analysis of polynucleotides comprising:

i) from about 7% to the solubility limit of at least one hydrophilic polymer;
ii) at least one denaturant; and
iii) at least one buffer.

63. The denaturing composition of claim 62 wherein said hydrophilic polymer is selected from the group consisting of dextran, polyethylene glycol, polyethylene oxide, cellulose derivatives, polyvinyl alcohol agarose, modifications of the foregoing, and mixtures of the foregoing.

64. The denaturing composition of claim 63 wherein the concentration of said hydrophilic polymers is between about 15% to about 50%.

65. The denaturing composition of claim 64 wherein said hydrophilic polymer is dextran having a molecular weight of at least about 750,000.

66. The denaturing composition of claim 62 wherein said denaturant is selected from the group consisting of
i) 6M to about 8M urea;
ii) a combination of between about 3M and about 8M urea and between about 20% and about 40% of a non-urea agent; and
iii) up to about 98% of a non-urea denaturing agent.

67. The denaturing composition of claim 62 wherein said denaturant is 7M urea.

68. The denaturing composition of claim 66 wherein the non-urea denaturing is represented by the following structure:

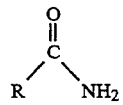

wherein R is selected from the group consisting of hydrogen, an alkyl chain having from 1 to about 6 carbon atoms, benzene ring and substituted benzene rings.

69. The denaturing composition of claim 68 when R is hydrogen.

70. The denaturing composition of claim 62 wherein the buffer has a pH of between about 7.0 and about 9.0.

71. The denaturing composition of claim 62 wherein the buffer has a pH of between about 8.0 and about 8.5.

72. The denaturing composition of claim 62 wherein the buffer has a pH of about 8.3.

73. The denaturing composition of claim 72 wherein the buffer is tris-hydroxymethyl amino-methane borate.

74. The denaturing composition of claim 62 wherein said denaturing composition comprises about 7M urea, about 20% dextran having a molecular weight of at least about 750,000, and a buffer having a pH of between about 8.0 and about 9.0.

75. A capillary column comprising:
a) a capillary column having an interior cavity defined by a wall with an inner surface;
b) at least one bifunctional agent adsorbed to the inner surface of the wall, said agent comprising at least one positively charged amine and at least one active functional group; and
c) at least one denaturing composition substantially interspersed throughout the remainder of the cavity, said denaturing composition comprising about 20% dextran, about 7M urea; and a buffer, wherein the pH of the composition is between about 8.0 and about 9.0.

* * * * *